United States Patent [19]

Hattner

[11] Patent Number: 5,342,926

[45] Date of Patent: Aug. 30, 1994

[54] ANALOGS OF CYTOCHALASIN B AS RADIOPHARMACEUTICALS FOR NUCLEAR IMAGING OF TRANS-MEMBRANE GLUCOSE TRANSPORT

[75] Inventor: Robert S. Hattner, Mill Valley, Calif.

[73] Assignee: The Regents of the University of California, Oakland, Calif.

[21] Appl. No.: 73,848

[22] Filed: Jun. 8, 1993

[51] Int. Cl.$^5$ .................... C07F 13/00; C07D 491/02
[52] U.S. Cl. ..................... 534/10; 548/431; 534/14
[58] Field of Search .............. 534/10, 14; 424/1.1, 424/1.85, 1.89, 165; 548/418, 431

[56] References Cited

U.S. PATENT DOCUMENTS

| | | | |
|---|---|---|---|
| 4,018,884 | 4/1977 | Cleeland, Jr. | 424/7 |
| 4,130,462 | 12/1978 | Rubenstein | 195/103.5 |
| 4,360,511 | 11/1982 | Baldwin | 424/1.5 |
| 4,363,793 | 12/1982 | Blau | 424/1 |
| 4,411,881 | 10/1983 | Tzodikov | 424/1.1 |
| 4,494,547 | 1/1985 | Myers | 128/659 |
| 4,647,446 | 3/1987 | Sargeant | 424/1.1 |
| 4,765,972 | 8/1988 | Safa et al. | 424/1.1 |
| 4,861,581 | 8/1989 | Epstein | 424/1.1 |
| 4,942,231 | 7/1990 | Mertens | 540/586 |
| 5,041,376 | 8/1991 | Gething | 435/72.3 |
| 5,045,303 | 9/1991 | Wilbur | 424/1.1 |
| 5,110,801 | 5/1992 | Leveen | 514/34 |
| 5,141,739 | 8/1992 | Jung | 424/4 |
| 5,154,913 | 10/1992 | de Paulis | 424/1.1 |

FOREIGN PATENT DOCUMENTS

| | | |
|---|---|---|
| 9013293 | 11/1990 | World Int. Prop. O. |
| 9302105 | 2/1993 | World Int. Prop. O. |

OTHER PUBLICATIONS

Graeme Bell, et al., "Molecular Biology of Mammalian Glucose Transporters", in: Diabetes Care, vol. 13, No. 3, Mar. 1990, pp. 198-208.

Bernard Thorens, et al., "Molecular Physiology of Glucose Transporters", in: Diabetes Care, vol. 13, No. 3, Mar. 1990, pp. 209-218.

Mary A. Kasanicki, Paul F. Pilch, "Regulation of Glucose-Transporter Function", in: Diabetes Care, vol. 13, No. 3, Mar. 1990, pp. 219-227.

Amira Klip, Michel R. Paquet, "Glucose Transport and Glucose Transporters in Muscle and Their Metabolic Regulation", in: Diabetes Care, vol. 13, No. 3, Mar. 1990; pp. 228-243.

Barbara B. Kahn, et al., "Regulation of Glucose-Transporter Gene Expression In Vitro and In Vivo", in: Diabetes Care, vol. 13, No. 6, Jun. 1990, pp. 548-564.

Timothy J. Tewson, et al., "F-Labeled 3-Deoxy-3--Fluoro-D-Glucose: Synthesis and Preliminary Biodistribution Data", in: Journal of Nuclear Medicine, vol. 19, No. 12, Dec. 1978, pp. 1339-1345.

(List continued on next page.)

*Primary Examiner*—Robert L. Stoll
*Assistant Examiner*—Lara E. Chapman
*Attorney, Agent, or Firm*—Townsend and Townsend Khourie and Crew

[57] ABSTRACT

Analogs of cytochalasin B are used as radiopharmaceuticals to provide an image for the nuclear imaging of glucose transport across cell membranes. Like cytochalasin B, the analogs bind specifically to glucose transport protein, and in doing so, serve as markers indicating the amount of glucose transport protein present on the surfaces of cells. The analogs differ from cytochalasin B by the inclusion of a radionuclide in the region of the terminal phenyl group on cytochalasin B, where the radionuclide does not interfere with the binding specificity of the analog. Disclosed herein are such analogs as well as analogs with which readily accept radionuclides at the desired location on the structure, either by conjugation or substitution.

7 Claims, No Drawings

OTHER PUBLICATIONS

Darryl C. De Vivo, et al., "Defective Glucose Transport Across The Blood-Brain Barrier As a Cause of Persistent Hypoglycorrhachia, Seizures, And Developmental Delay", in: New England Journal of Medicine, vol. 325, No. 10, Sep. 5, 1991, pp. 703-709.

S. Masamune, et al., "Activation of Thiol Esters. Partial Synthesis of Cytochalasins A and B" in: Journal of the American Chemical Society, 99, 6756 (1977).

Gilbert Stork, et al., "Total Synthesis of Cytochalasin B", in: Journal of the American Chemical Society, 100:24, Nov. 22, 1978, pp. 7775-7777.

De Vivo et al., "Defective glucose Transport..." *New England Journal of Medicine,* vol. 325, No. 10, Sep. 5, 1991, pp. 703-709.

Masamune et al. "Activation of Thiol Esters..." *Jouranl of American Chemical Society,* 99, 6756 (1977), pp. 6756-6758.

Stork et al., "Total Synthesis of Cytochalasin B", *Journal of American Chemical Society,* 100:24 (1978) pp. 7775-7777.

ANALOGS OF CYTOCHALASIN B AS RADIOPHARMACEUTICALS FOR NUCLEAR IMAGING OF TRANS-MEMBRANE GLUCOSE TRANSPORT

This invention lies in the field of nuclear medicine and of radiopharmaceuticals used in nuclear imaging procedures.

BACKGROUND OF THE INVENTION

The rate of glucose metabolism by a living cell is known to be a useful indicator of a variety of abnormal physiological conditions, particularly in human patients. Included among these conditions are various forms of cancer, coronary artery disease, brain tumors and epilepsy. The diagnosis and locale determination of these conditions has been made possible by sophisticated imaging techniques that identify cells which are demonstrating abnormally high or low rates of glucose intake.

Imaging up until now has been performed by positron-emission tomography (PET) with glucose analogs such as carbon-11-labeled glucose and $^{18}$F-labeled 2-deoxy-2-fluoro-D-glucose and its isomer $^{18}$F-labeled 3-deoxy-3-fluoro-D-glucose (the last two are referred to as "2-FDG" and "3-FDG," respectively). The analogs, upon administration to the patient prior to the imaging procedure, enter the cell in the same manner as glucose, and the resulting whole body distribution of the analogs as detected by the imaging procedure indicates the stage and locus of the abnormality. These are the only known analogs which will achieve transport across the cell membrane in the same manner as glucose, because derivatization of the glucose molecule destroys the receptor specificity of the molecule, thereby interfering with its transport. PET is the imaging technique of choice because it is sensitive enough to usefully detect the annihilation photons emitted by these analogs. The advantage of the FDG's over carbon-11-labeled glucose is that, unlike the carbon-11-labeled glucose, the FDG's do not complete the metabolic cycle inside the cells, and therefore remain in the cells long enough for imaging to take place.

Unfortunately, PET is one of the more costly imaging procedures. As a result, nuclear medicine scanning based on glucose transport abnormalities has enjoyed only limited use, and is feasible only at locations where PET equipment is available. This has hindered the development of glucose transport both as a research tool and as a diagnostic method.

SUMMARY OF THE INVENTION

The present invention provides for nuclear imaging of glucose transport levels based on the interaction of glucose transport protein and cytochalasin B. This invention differs from the prior art by associating the labeled species with the cell membrane rather than with the cell interior. The labeled species in this case is an analog of cytochalasin B which bears a radiolabel in a location which does not interfere with the interaction between cytochalasin B and glucose transport protein.

Glucose transport protein is any of five proteins present on the membranes of cells of the brain and other tissues in the body which metabolize glucose. These proteins are highly similar in structure and each functions to facilitate the diffusion of glucose across the cell membrane. The differences among these proteins are post-translationally imposed, and are on portions of the proteins other than those responsible for the glucose transport. In this specification, the term "glucose transport protein" is used to refer to any of the individual known glucose transport proteins.

The amount of glucose transport protein present on the surface of a cell is changeable and varies with the cell's demand for glucose. A high demand for glucose, for example, which is a characteristic of malignant cells, is responded to by a high concentration of glucose transport protein on the cell membrane surface. Certain brain disorders, on the other hand, such as epilepsy and delayed development, are the result of a defect or deficiency in the glucose transport protein.

Cytochalasin B is the most important and most biologically studied of the cytochalasins, which are a class of mold metabolites. Cytochalasin B is obtainable from cultures of a Phoma sp. of mold, and for this reason bears the generic name "phomin." The formula for cytochalasin B is as follows:

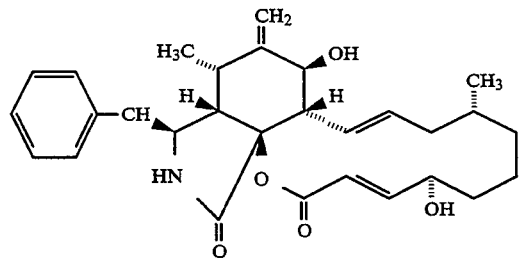

A characteristic of cytochalasin B is that it specifically binds to glucose transport protein. The binding site is sufficiently removed from the phenyl ring, however, that variations of, and substitutions on, the phenyl ring do not affect the binding interaction between cytochalasin B and glucose transport protein. In accordance with the present invention, therefore, an imaging agent for nuclear imaging is provided by derivatizing a cytochalasin B molecule to contain a radionuclide on or near the phenyl ring.

Since structural modifications in the region of the phenyl ring do not affect the specific binding characteristics of the cytochalasin B, analogs bearing radioactive labels of many types can be prepared, all of which will bind to glucose transport protein in the same manner as cytochalasin B. Radioimaging to detect the level and distribution of glucose metabolism is thus no longer limited to PET, but can also be done by nuclear scanning methods which require lower energy single photon emitters. Furthermore, unlike imaging methods which use an FDG as an imaging agent, imaging with these cytochalasin B analogs does not rely on the agent entering the cell, and is thus not in competition with, or otherwise affected by, the glucose which is also present in the tissue.

Accordingly, the invention resides in novel radiopharmaceuticals which are cytochalasin B analogs. These analogs are identical to cytochalasin B except that the phenyl ring of cytochalasin B is either substituted with a radionuclide or replaced by a radionuclide or a group which includes a radionuclide. The invention further resides in stable (nonradioactive) cytochalasin B analogs which differ from cytochalasin B in the same region as do the radiopharmaceuticals but which are readily convertible to the radiopharmaceuticals by simple chemical reactions. With these stable analogs as starting materials, the conversion reactions can be performed on site shortly before administration of the radiopharmaceuticals for imaging purposes. Still further, the invention resides in methods for detecting and imaging levels of glucose transport protein as a measure of the distribution of glucose metabolism in the body of a patient.

Other features and advantages of the invention will be apparent from the description which follows.

DETAILED DESCRIPTION OF THE INVENTION AND PREFERRED EMBODIMENTS

Cytochalasin B analogs useful in the practice of the invention are those of the formula

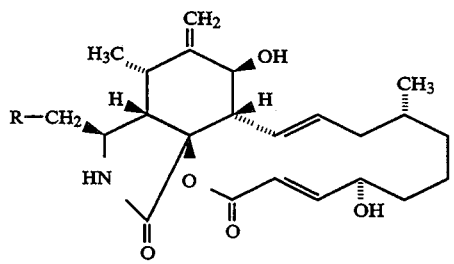

in which R is either:
a radionuclide,
an aliphatic or alicyclic group containing a radionuclide,
a phenyl ring substituted with a radionuclide,
a phenyl ring substituted with a nonradioactive group which will facilitate the substitution of a radionuclide at another location on the phenyl ring by a reaction such as a Bolton-Hunter reaction,
a phenyl ring substituted with a nonradioactive group which is replaceable by a radionuclide through a simple chemical reaction such as an exchange reaction or a Sandmeyer reaction,
a conjugate of a radionuclide, or
a non-radioactive conjugating group which is capable of accepting a radionuclide by conjugation. Thus, the symbol R represents two classes of substituents—(1) those which are or contain radionuclides, in which case the analog is already a radiopharmaceutical and ready for administration to a subject for an imaging procedure; and (2) those which are nonradioactive precursors to which radionuclides are readily joined either by covalent bonds, electronic interaction or steric retention, either through conjugation or substitution. Examples of reactions by which the nonradioactive analogs of the above formula can be converted to radiopharmaceuticals are chelation reactions, exchange reactions, and electrophilic substitutions. For analogs which are themselves radiopharmaceuticals, examples of R for radiopharmaceuticals are:
monovalent radionuclides, aliphatic, alicyclic and aromatic groups containing monovalent radionuclide substituents,
aliphatic, alicyclic and aromatic groups containing polyvalent radionuclide substituents, and
radionuclide conjugates, including chelates of radionuclides and other ligand-bonded radionuclide structures.
Primary examples of aliphatic groups are alkyl groups such as straight-chain $C_1$–$C_4$ alkyls; primary examples of alicyclic groups are saturated $C_5$–$C_7$ cycloalkyls; and the primary example of an aromatic group is a phenyl group. Depending on its valence, the radionuclide may either be a substitute for a hydrogen atom or a link in an otherwise carbon chain in the alkyl, alicyclic or aromatic structure. In preferred embodiments, R is either a radiohalogen-substituted phenyl group, a chelate of a gamma-ray-emitting radionuclide, or a ligand-bonded radionuclide such as ligands known to be useful for technetium.

For embodiments in which R is a chelate, the chelating ligand may be any of the wide variety of such ligands well known among those in nuclear medicine and chelate chemistry. Examples of chelating ligands are diethylenetriamine pentaacetic acid (DTPA), ethylenediamine tetraacetic acid, nitrilotriacetic acid (NTA), and ethylene glycolbis-bis($\beta$-aminoethyl ether)-N,N-tetraacetic acid. Examples of ligands to which technetium can be conjugated are diamino dimercaptide and hydrazinonicotinamide. The derivatization and attachment of these ligands to the phenyl ring of the analog are matters of routine chemistry well known among those skilled in the art.

Examples of preferred atoms and groups for R in those embodiments in which the analog is a radiopharmaceutical are phenyl rings containing $^{121}I$, $^{122}I$, $^{123}I$, $^{124}I$, $^{125}I$, $^{131}I$, $^{74}Br$, $^{75}Br$, $^{76}Br$, $^{77}Br$, $^{34m}Cl$, $^{18}F$ or $^{211}At$, and chelates of (or ligands bearing) $^{99m}Tc$, $^{111}In$, $^{113m}In$ and $^{67}Ga$. Among these, particularly preferred are $^{121}I$, $^{122}I$, $^{123}I$, $^{124}I$, $^{125}I$, and $^{131}I$. The most preferred is $^{123}I$.

For those embodiments of the invention in which the analog is a precursor to a radiopharmaceutical rather than a pharmaceutical itself, R is either a chelating ligand (which term is used herein to include technetiatable ligands), a phenyl ring substituted with an electrophilic activating atom or group which activates the phenyl ring for acceptance of a radionuclide, or a phenyl ring substituted with an atom or group which is convertible by a simple chemical reaction or series of reactions to a radionuclide or a group which contains a radionuclide. Examples of electrophilic activating groups are a hydroxyl group, a nitro group, an amino group and an amido group. The term "amido" is used herein to include formamido, acetamido, propionamido, and higher alkylated homologs. An example of a reaction by which a nonradioactive analog bearing an electrophilic activating group can be converted to a radiopharmaceutical is the Bolton-Hunter reaction, where the electrophilic activating group permits substitution of a halogen at a position either ortho- or para- to the activating group, using the halogen in diatomic molecular form in the presence of a suitable solvent. A particularly preferred electrophilic activating group in this category is a hydroxyl group. For groups which are replaceable by radionuclides through simple chemical reactions, an example is the amino group, which can be oxidized to a diazonium group, then converted to a halogen by a reaction such as a Sandmeyer reaction, a Gattermann reaction or a Körner-Contardi reaction. A further example of a group readily replaceable by a radionuclide is a stable halogen, which can be substituted by a radioactive isotope of the same halogen by a simple exchange reaction. A particularly preferred stable halogen for this purpose is $^{127}I$, which can readily be replaced by $^{123}I$ with an appropriate exchange reaction.

For nonradioactive analogs of this invention in which R is a phenyl ring bearing an electrophilic activating group, the preferred position of the electrophilic activating group on the phenyl ring is the ortho-position. A prime example of R within this subclass is ortho-hydroxy phenyl. For nonradioactive analogs in which R is a phenyl ring bearing a group replaceable by a radionuclide such as a radioactive halogen, the preferred position of replaceable group on the phenyl ring is the meta-position. Prime examples of R within this subclass are meta-iodo phenyl and meta-amino phenyl. Likewise, for radiopharmaceuticals within this invention in which R is a phenyl ring bearing a radionuclide, the preferred position of the radionuclide on the phenyl ring is the meta-position.

This invention further extends to analogs in which R is a phenyl ring containing additional substituents other than the radionuclide, electrophilic activating group or replaceable group, which additional substituents do not significantly detract from the utility of the analogs as radiopharmaceuticals or radiopharmaceutical precursors.

The analogs of the present invention may be prepared from biologically derived cytochalasin B, with appropriate derivatization, or by synthesis from simpler starting materials. A synthesis of a typical analog within the scope of the invention, based on the syntheses of Stork, G., et al., J. Am. Chem. Soc. 100(24):7775–7 (1978) and Masamune, S., et al., J. Am. Chem. Soc. 99:6756–8 (1977) is described in the succeeding paragraphs. In this synthesis, R is represented by a phenyl group bearing a substituent X, which may be a radionuclide, an electrophilic activating group, or an atom or group replaceable by a radionuclide. The symbol "AcO" denotes the acetate group. All reactions in this synthesis are conventional reactions for which detailed methods will be known to those skilled in the art of synthetic organic chemistry. Literature references are supplied in some cases as examples of sources in which these reactions are described.

The starting material is the acetate of pure citronellol 1. This is converted by treatment with $O_3$, $CH_2Cl_2$, and Zn dust/acetic acid to the crude aldehyde, which is then converted by a Jones oxidation to the acetate of 4(R)-methyl-6-hydrohexanoic acid 2. This product is then reacted with the 1-ethyl ester of (+)-malic acid 3 by a Kolbe electrolytic coupling reaction (as described by Horn, D. H. S., and Y. Y. Pretorius, J. Chem. Soc. 1460 (1954)), utilizing 0.2% ethanolic sodium ethoxide at about 1.5 A, at 45–50° C. for 75 minutes, followed by solvent removal and reacetylation of the crude mixture. The coupling product, which is the diacetate of ethyl 2-(R),8-dihydroxy-6(R)-methyloctanoate 4, is isolated in this reaction by elution. Reduction of the coupling product with $LiAlH_4$ in ether gives 6(R)-methyl-2(R)-1,2,8-octanetriol 5, which is converted to the triacetate 6 in silica gel, 4:1 hexane-ethyl acetate. The triacetate is converted to the acetonide by reaction with acetone and p-toluenesulfonic acid at room temperature for 3 hours, and the acetonide is converted by Collins oxidation for 1 hour at room temperature to the aldehyde 7.

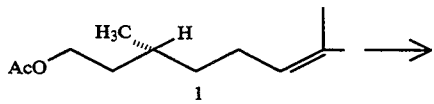

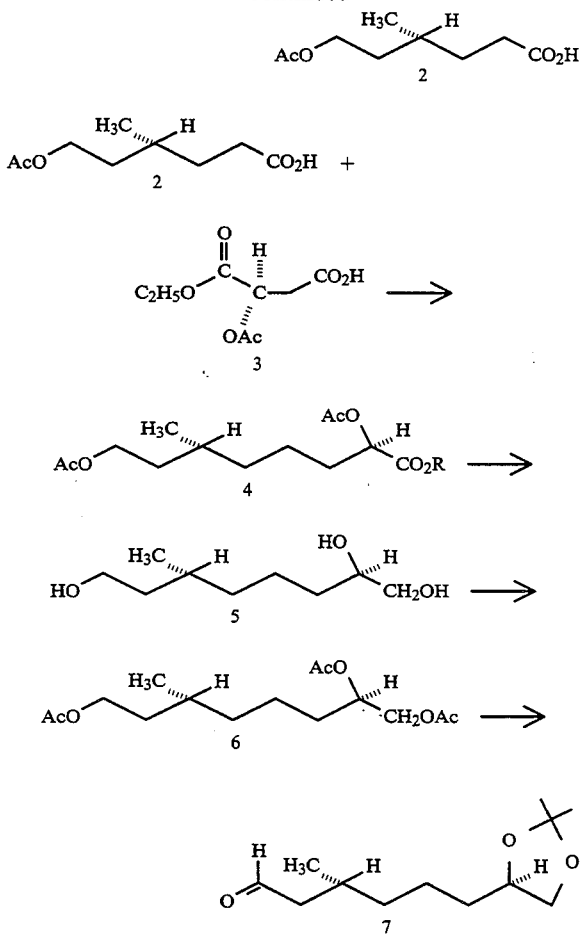

A trans,trans-dienic compound, for coupling with the aldehyde 7, is prepared as follows.

Glycidaldehyde 8 is condensed with carboxymethylene triphenylphosphorane (30% excess in benzene, 1.5-hour reflux) to give the unsaturated ester 9. The ester is then treated with formic acid for thirty minutes, followed by concentration under vacuum, overnight treatment with aqueous saturated bicarbonate, washing in hexane, and ethyl acetate extraction, to form the glycol 10. The primary alcohol on 10 is then protected as the tert-butyl dimethylsilyl ether and, after separation from some disilylated compound, is oxidized by $CrO_3\cdot 2C_5H_5N$ to the unsaturated keto ester 11. The ester is then condensed with ethylidenetriphenylphosphorane in tetrahydrofuran at −78° C. for 45 minutes, to give a 5.7:1 ratio of the desired trans,trans-dienic ester 12 and its trans,cis-isomer, with separation of the two readily accomplished by elution with 3% ethyl acetate in hexane, since the trans,cis-isomer is more easily eluted. Reduction of the trans,trans-dienic ester 12 with sodium bis(methoxyethoxy)aluminum hydride gives the corresponding alcohol 13. The alcohol is then dissolved in 3:1 ether-hexamethylphosphoramide and treated with butyllithium at −30° C., followed by p-toluenesulfonyl chloride, and, after thirty minutes, by sodium diethyl phosphite in toluene, to form the dienyl phosphonate 14.

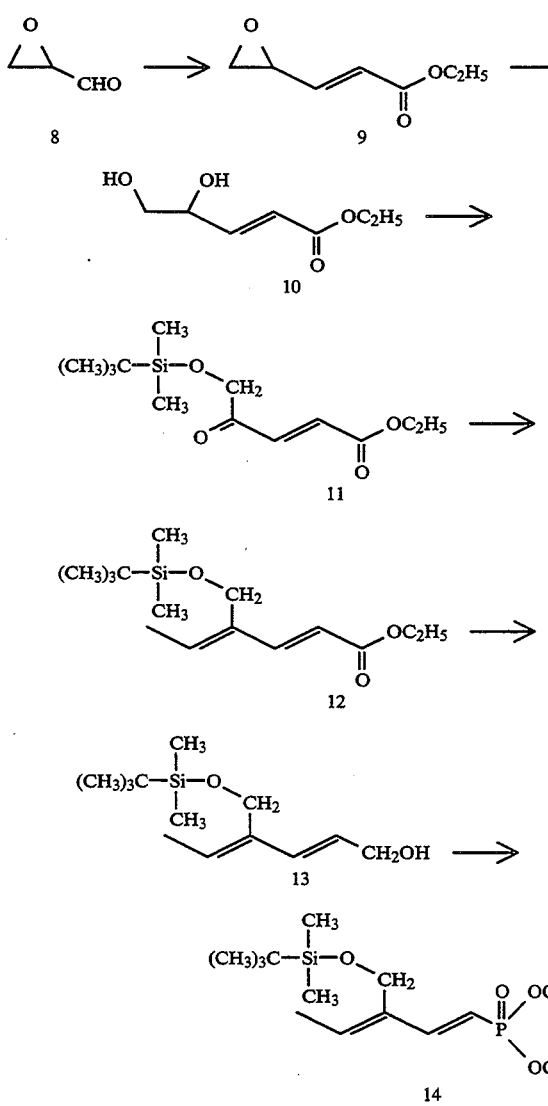

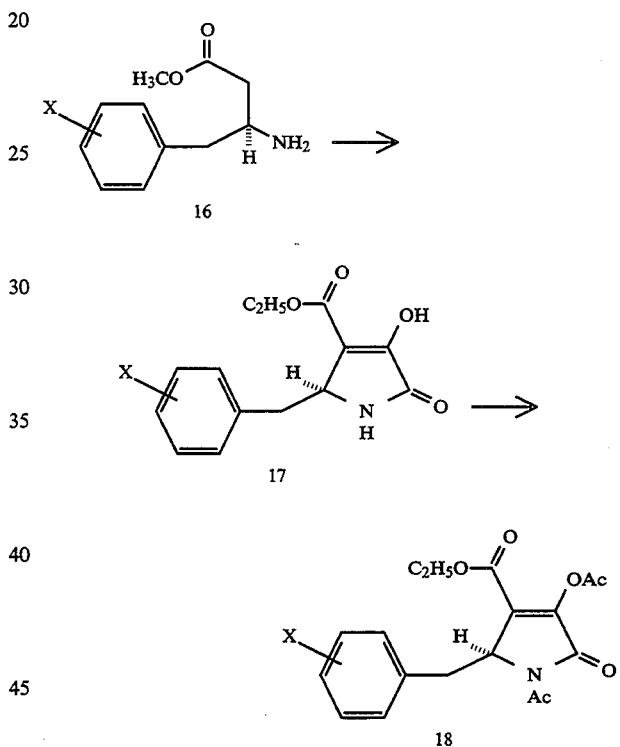

16 is converted into the hydroxypyrrolone ester 17 by the method of Southwick, P. L., and R. T. Crouch, J. Am. Chem. Soc. 75:3413 (1953). The hydroxypyrrolone ester 17 is then treated with acetic anhydride-pyridine, with 4-N,N-dimethylaminopyridine as catalyst, for thirty minutes at room temperature, followed by hydrolysis-decarboxylation, using dimethyl sulfoxide-sodium chloride-water (50:28: 1), at 135°–140° C. for 1.5 hours in a nitrogen atmosphere. The liberated hydroxyl is then reacetylated, and the N-acetyl pyrrolone acetate 18 is isolated by chromatography on silica, using 4:1 hexane-ethyl acetate followed by 3:2 chloroform-ethyl acetate.

The dienyl phosphonate 14 is converted to its sodium salt by reaction with sodium hydride in benzene, with 0.25 equivalents of methanol for two hours at 55° C., and then condensed with the aldehyde 7 at 55° C. overnight, to form the desired triene 15:

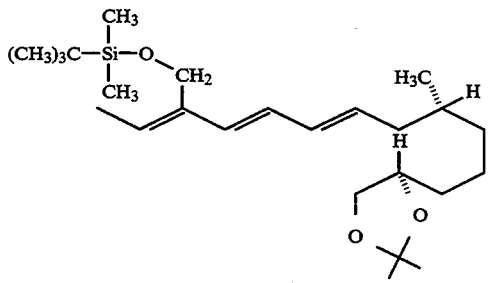

A pyrrolone to act as a dienophile for cycloaddition to the triene 15 is prepared as follows. Methyl L-3-amino-(substituted phenyl)butyrate 16 is prepared from the appropriately substituted N-carbobenzoxy-L-alanine by Arndt-Eistert homologation, via the silver oxide-methanol rearrangement of the diazo ketone, followed by 10% Pd/C hydrogenolysis. The amino ester Cycloaddition of the triene 15 to the N-acetyl pyrrolone acetate 18 is performed in xylene at 170° C. over 4 days, to form the adduct 19. The silyl protecting group of the adduct 19 is then removed by treatment with 3:1:1 acetic acid-water-tetrahydrofuran, at room temperature overnight, followed by acetone-p-toluenesulfonic acid for 1.5 hours at room temperature, to yield the unprotected compound 20. The unprotected compound is then treated with tert-butyl hydroperoxide and Mo(CO)$_6$, under reflux in benzene for 1.5 hours, to yield the epoxide 21, which is then treated with carbon tetrabromide and triphenylphosphine for 4 hours at room temperature, to yield the bromide 22, followed by β-elimination using zinc dust/sodium iodide to give the 2-hydroxy-1-methylenecyclohexane compound 23.

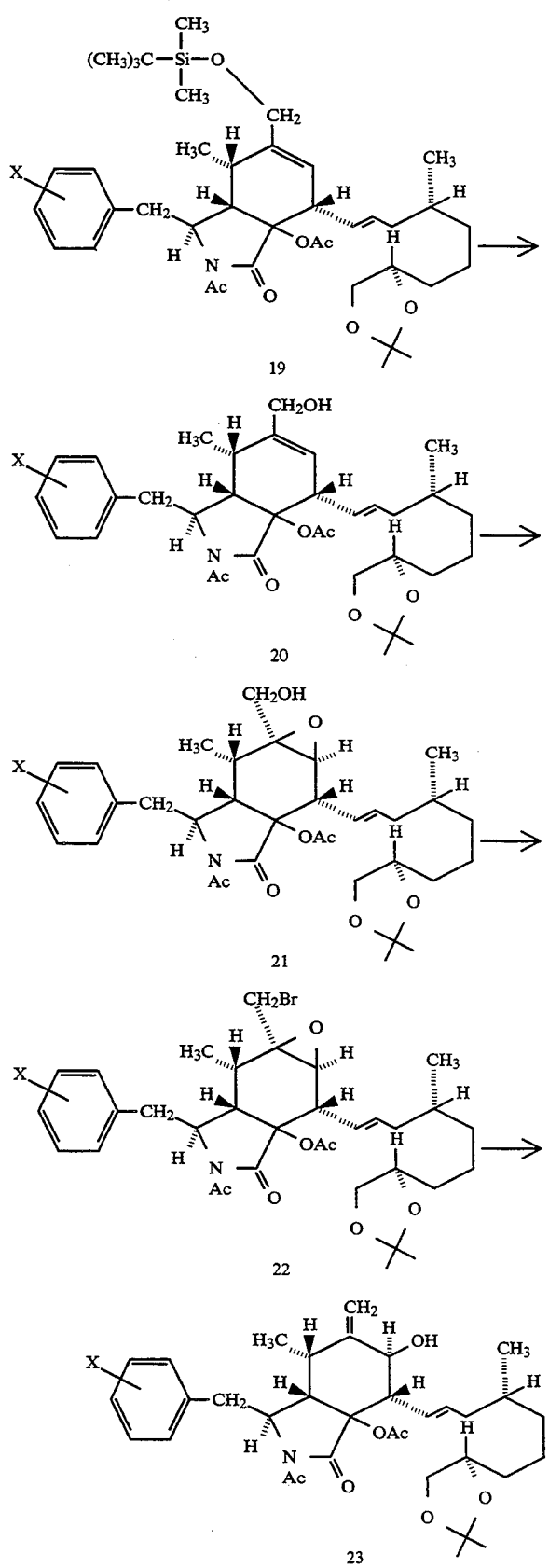

acetic acid-tetrahydrofuran for 4 hours at room temperature to liberate the 1,2-glycol, leaving the primary alcohol 24. The primary alcohol is then protected as the tert-butyl dimethylsilyl ether 25, and the two secondary hydroxyls are protected as the tetrahydropyranyl ethers 26. The primary alcohol 27 is then liberated by treatment with tetrabutylammonium fluoride, followed by oxidation to the aldehyde 28 using a Collins reaction, and condensation with methyltriphenylphosphoranylidene acetate to yield the 4-hydroxy trans-α,β-unsaturated ester 29. The ester is then treated with 1 N ethanolic sodium hydroxide at 60° C. for 1 hour, followed by chromatography on silica with 9:1 $CHCl_3$—$CH_3OH$ to yield the hydroxy unsaturated acid 30. The hydroxy unsaturated acid is subsequently cyclized by being heated with $Na_2HPO_4$ and $AgCF_3CO_2$ in benzene at reflux under an argon atmosphere, followed by mild alkaline hydrolysis. The product is the cytochalasin B analog of the present invention.

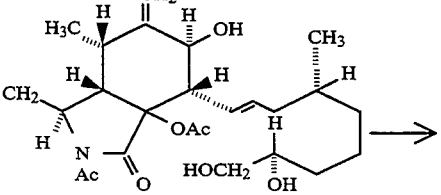

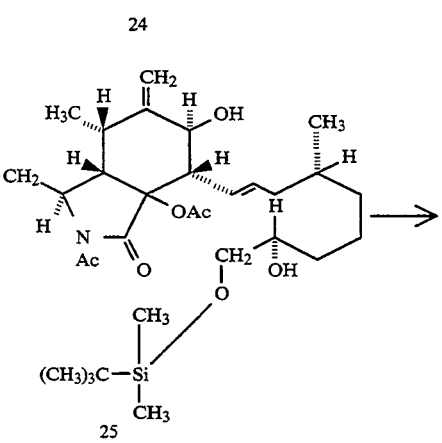

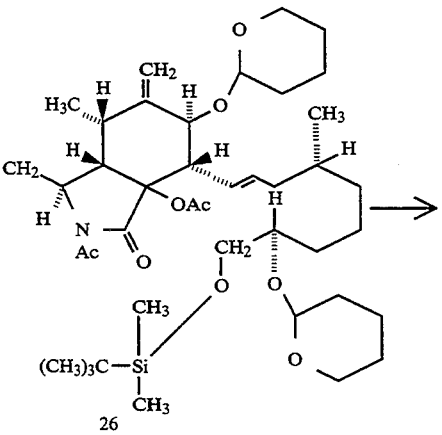

To convert the terminal isopropylidene group of the 2-hydroxy-1-methylene-cyclohexane compound 23 to a 4-hydroxy trans-a,β-unsaturated ester system, the terminal isopropylidene group is reacted with aqueous -continued

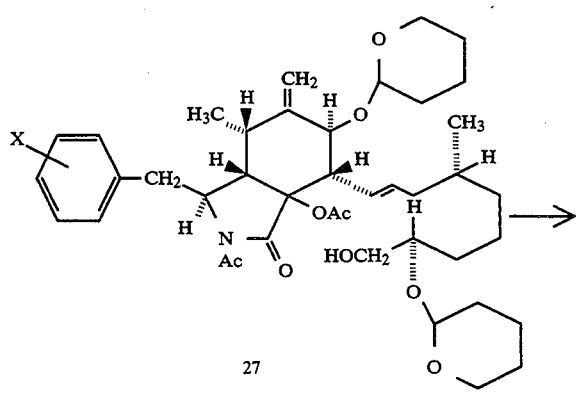

27

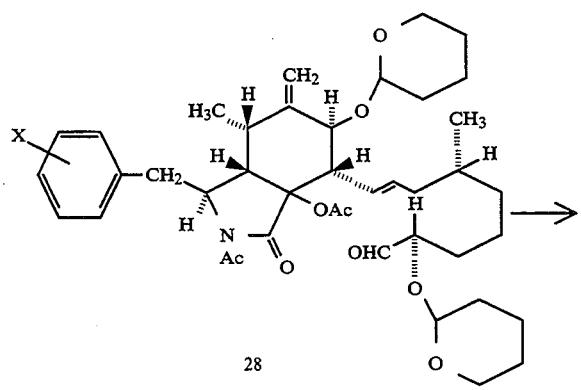

28

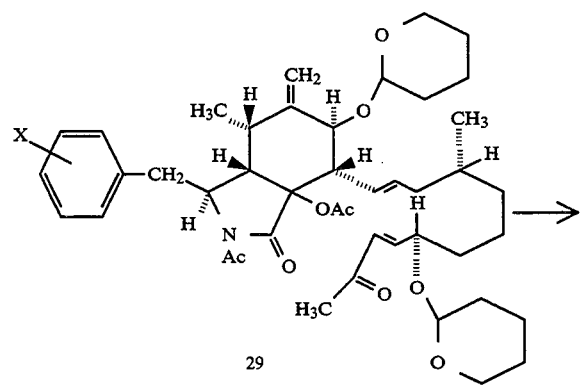

29

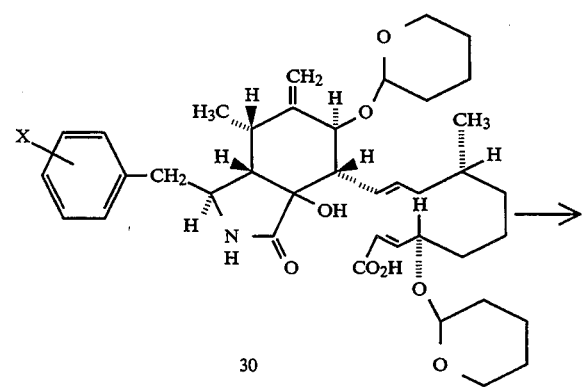

30

-continued

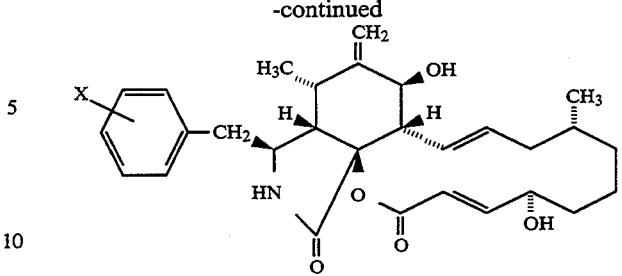

Cytochalasin B Analog

The placement of X on the phenyl ring of the N-carbobenzoxy-L-alanine used in the preparation of the methyl L-3-amino-(substituted phenyl) butyrate 16 is achieved by conventional methods. In preparing nonradioactive precursors to the radiopharmaceuticals, it is preferred to begin the synthesis with an N-carbobenzoxy-L-alanine already bearing the X substituent. Conversion to a radiopharmaceutical is then performed on the otherwise fully synthesized analog. To place radioactive halogens on the ring, for example, a variety of methods can be used. Starting with a nonradioactive analog bearing an amine group on the phenyl ring, the amine group can be oxidized to a diazonium group, which is then replaced by a radioactive halogen such as fluorine either in the presence of cuprous salts (Sandmeyer reaction), copper powder (Gattermann reaction) or cupric salts (Körner-Contardi reaction). Radiopharmaceuticals bearing radioactive bromine can be derived from a nonradioactive analog bearing an ortho-hydroxy group as X, by treating the analog with molecular bromine in the presence of acetic acid, Fe metal, carbon disulfide or t-butylamine, using a Bolton-Hunter reaction. With an ortho-hydroxy group as X, substitution of the halogen at the meta-position can be achieved by a Bolton-Hunter reaction, using a molecular halogen and either carbon disulfide or tributylamine and toluene at low temperatures. Nonradioactive analogs bearing stable halogens as X can be converted to radiopharmaceuticals by substituting the stable halogen with a radioactive halogen, using an exchange reaction according to well-known techniques.

The preparation of analogs in which R is a chelate or other conjugating ligand rather than a substituted phenyl ring is achieved by using the ligand substituted with methyl L-3-aminobutyrate in place of the methyl L-3-amino-(substituted phenyl)butyrate 16. Methods of preparing ligands substituted in this manner are known among those skilled in synthetic chemistry.

The conversion of a nonradioactive analog within the scope of this invention to a radiopharmaceutical can be performed by the user shortly prior to administration to a patient, or by a central processing facility located in close proximity to a diagnosis laboratory in a hospital or clinic. Other arrangements for forming and using the compounds will be readily apparent to clinicians, technicians and doctors who are experienced in imaging procedures and techniques.

Administration of the cytochalasin B analogs of the present invention for purposes of nuclear imaging is achieved by conventional procedures. Aqueous solutions of the analogs, and in particular, solutions in physiological saline, are most conveniently used. The concentrations of the analogs in these solutions and the amounts administered may vary widely, the optimum in each case varying with the strength of the radionuclide in the analog, the method of administration, the degree of activity uptake desired or needed, and the age, weight and condition of the patient or subject to whom administration is made. A typical dose for an adult human is approximately 2.5 milligrams of the radiopharmaceutical in physiological saline at a concentration of 5 µM, or approximately 35 µg per kg of the subject's whole body weight. In terms of the radionuclide such as $^{123}$I, a typical dose would be 5–10 millicuries. Administration may be achieved by any parenteral route and method, most notably by intravenous administration.

The cytochalasin B analogs of this invention are useful in a wide range of imaging techniques. Examples are conventional diagnostic gamma-ray camera imaging and more complex techniques such as single photon emission computed tomography (SPECT) and positron emission tomography (PET).

The foregoing is offered primarily for purposes of illustration. It will be readily apparent to those skilled in the art that the descriptions of the preferred pharmaceutical agents and administration methods described herein may be further modified in various ways without departing from the spirit and scope of the invention.

What is claimed is:

1. A compound having the formula

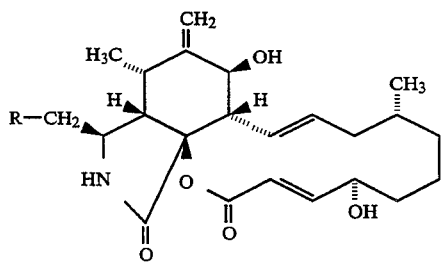

in which R is a member selected from the group consisting of:
a radionuclide,
an aliphatic or alicyclic group containing a radionuclide,
a phenyl ring substituted with a radionuclide, and
a chelate of a radionuclide
said radionuclide being selected from the group consisting of $^{121}$I, $^{122}$I, $^{123}$I, $^{124}$I, $^{125}$I, $^{131}$I, $^{74}$Br, $^{75}$Br, $^{76}$Br, $^{77}$Br, $^{34m}$Cl, $^{18}$F, $^{211}$At, $^{99m}$Tc, $^{111}$In, $^{113m}$In and $^{67}$Ga.

2. A compound in accordance with claim 1 in which R is a member selected from the group consisting of:
phenyl rings containing monovalent radionuclide substituents, and
chelates of a radionuclide.

3. A compound in accordance with claim 1 in which R is a member selected from the group consisting of:
a phenyl ring containing a substituent which is a member selected from the group consisting of $^{121}$I, $^{122}$I, $^{123}$I, $^{124}$I, $^{125}$I, $^{131}$I, $^{74}$Br, $^{75}$Br, $^{76}$Br, $^{77}$Br, $^{34m}$Cl, $^{18}$F and $^{211}$At, and
a chelate of a member selected from the group consisting of $^{99m}$Tc, $^{111}$In, $^{113m}$In and $^{67}$Ga.

4. A compound in accordance with claim 1 in which R is a member selected from the group consisting of:
a phenyl ring substituted in the meta-position with a member selected from the group consisting of $^{121}$I, $^{122}$I, $^{123}$I, $^{124}$I, $^{125}$I, $^{131}$I, $^{74}$Br, $^{75}$Br, $^{76}$Br, $^{77}$Br, $^{34m}$Cl, $^{18}$F and $^{211}$At,
a chelate of a member selected from the group consisting of $^{111}$In, $^{113m}$In and $^{67}$Ga, in which the chelating ligand is a member selected from the group consisting of diethylenetriamine pentaacetic acid, ethylenediamine tetraacetic acid, nitrilotriacetic acid, and ethylene glycol-bis(β-aminoethyl ether)-N, N- tetraacetic acid,
technetium diamino dimercaptide, and
technetium hydrazinonicotinamide.

5. A compound in accordance with claim 1 in which R is a member selected from the group consisting of:
a phenyl ring substituted in the meta-position with a member selected from the group consisting of $^{121}$I, $^{122}$I, $^{123}$I, $^{124}$I, $^{125}$I, and $^{131}$I,
a chelate of a member selected from the group consisting of $^{111}$In, $^{113m}$In and $^{67}$Ga, in which the chelating ligand is a member selected from the group consisting of diethylenetriamine pentaacetic acid and nitrilotriacetic acid,
technetium diamino dimercaptide, and
technetium hydrazinonicotinamide.

6. A compound in accordance with claim 1 in which R is a phenyl ring substituted in the meta-position with a member selected from the group consisting of $^{121}$I, $^{122}$I, $^{123}$I, $^{124}$I, $^{125}$I, and $^{131}$I.

7. A compound in accordance with claim 1 in which R is a phenyl ring substituted in the meta-position with $^{123}$I.

* * * * *